US006214851B1

(12) United States Patent
Duncia et al.

(10) Patent No.: US 6,214,851 B1
(45) Date of Patent: Apr. 10, 2001

(54) N-ADAMANT-1-Y1-N1-[4-CHLOROBENZOTHIAZOL-2-Y1] UREA USEFUL IN THE TREATMENT OF INFLAMMATION AND AS AN ANTICANCER RADIOSENSITIZING AGENT

(75) Inventors: John J. V. Duncia, Hockessin; Daniel S. Gardner, IV, Wilmington, both of DE (US); Joseph B Santella, III, Springfield, PA (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/527,331

(22) Filed: Mar. 17, 2000

Related U.S. Application Data

(60) Provisional application No. 60/125,331, filed on Mar. 19, 1999.

(51) Int. Cl.$^7$ .................................... A61K 31/425
(52) U.S. Cl. ..................... 514/367; 548/160; 548/163
(58) Field of Search .................... 514/367; 548/160, 548/163

(56) References Cited

U.S. PATENT DOCUMENTS

| 3,682,922 | 8/1972 | Klimstra . |
| 5,099,021 | 3/1992 | Worther et al. . |

FOREIGN PATENT DOCUMENTS

| 0612741 | 8/1994 | (EP) . |
| 9212141 | 7/1992 | (WO) . |
| 9743251 | 11/1997 | (WO) . |

OTHER PUBLICATIONS

Duncia et al, MEK Inhibitors: The Chemistry and Biological Activity of U0126, its Analogs, and Cyclization Products, 1998, pp. 2839–2844.
Biochem J. (1995) 309, 361–375.
Biochem J. (1997) 326, 867–876.
Biochem J. (1998) 330, 1107–11114.
Biochem. Biophy. Res. Commun. (1997) 232, 474–477.
Eur. J. Biochem. (1995) 228, 1–15.
FEBS Lett. (1996) 338, 180–184.
FEBS Lett. (1993) 334, 189–192.
J. Biol. Chem. (1993) 268, 14553–14556.
J. Biol. Chem. (1995) 270, 27391–27394.
J. Biol. Chem. (1995) 46, 27498–27494.
J. Biol. Chem. (1997) 272, 16709–16712.
J. Biol. Chem. (1997) 272, 13397–13402.
J. Biol. Chem. (1998) 29, 18623–18632.
J. Immunol. (1997) 159, 5070–5078.
J. Immunol. (1998) 160, 2579–2589.
J. Immunol. (1998) 160, 4175–4181.
Proc. Natl. Acad. Sci. USA (1995) 92, 1614–1618.
Proc. Natl. Acad. Sci. USA (1995) 92, 7686–7689.

*Primary Examiner*—James H Reamer
(74) *Attorney, Agent, or Firm*—Rosemarie Wilk-Orescan; Kenneth Rubin

(57) ABSTRACT

This invention relates generally to N-adamant-1-yl-N'-[4-chlorobenzothiazol-2-yl] urea, pharmaceutical compositions comprising the same, and methods of using the same in the treatment of inflammation and as an anticancer radiosensitizing agent.

7 Claims, No Drawings

N-ADAMANT-1-Y1-N1-[4-CHLOROBENZOTHIAZOL-2-Y1] UREA USEFUL IN THE TREATMENT OF INFLAMMATION AND AS AN ANTICANCER RADIOSENSITIZING AGENT

This application claims the benefit of U.S. Provisional Application No. 60/125,331, filed Mar. 19, 1999.

FIELD OF THE INVENTION

This invention relates generally to N-adamant-1-yl-N'-[4-chlorobenzothiazol-2-yl] urea, pharmaceutical compositions comprising the same, and methods of using the same in the treatment of inflammation and as an anticancer radiosensitizing agent.

BACKGROUND OF THE INVENTION

The mitogen activated protein kinase (MAPK) signaling pathways are involved in cellular events such as growth, differentiation and stress responses (*J. Biol. Chem.* (1993) 268, 14553–14556). Four parallel pathways have been identified to date: ERK1/ERK2, JNK, p38 and ERK5. These pathways are linear kinase cascades in that MAPKKK phosphorylates and activates MAPKK that phosphorylates and activates MAPK. To date, there are 7 MAPKK homologs (MEK1, MEK2, MKK3, MKK4/SEK, MEK5, MKK6, and MKK7) and 4 MAPK families (ERK1/2, JNK, p38, and ERK5). The MAPKK family members are unique in that they are dual-specific kinases, phosphorylating MAPKs on threonine and tyrosine. Activation of these pathways regulates the activity of a number of substrates through phosphorylation. These substrates include transcription factors such as TCF, c-myc, ATF2 and the AP-1 components, fos and Jun; the cell surface components EGF-R; cytosolic components including PHAS-I, p90$^{rsk}$, cPLA$_2$ and c-Raf-1; and the cytoskeleton components such as tau and MAP2.

The prototypical mitogen activated protein kinase cascade is reflected by the ERK pathway (*Biochem J.* (1995) 309, 361–375). The ERK pathway is activated primarily in response to ligation of receptor tyrosine kinases (RTKs) (*FEBS Lett.* (1993) 334, 189–192). Signal propagation from the RTKs occurs down the Ras pathway through sequential phosphorylation of Raf, MEK and ERK. This pathway has not been typically viewed of as an important contributor to the inflammatory response, but rather involved in growth and differentiation processes. This view stems from the profile of typical activators of this pathway, which include growth factors (PDGF, NGF, EGF), mitogens (phorbol esters), and polypeptide hormones (insulin, IGF-1). Evidence for ERK pathway involvement in inflammatory and immune responses has, however, gained some support in recent years (*Proc. Natl. Acad. Sci. USA.* (1995) 92, 1614–1618; *J. Immunol.* (1995) 155, 1525–1533; *J. Biol. Chem.* (1995) 270, 27391–27394; and *Eur. J. Biochem.* (1995) 228, 1–15). Cytokines such as TNFa and IL-1b, the bacterial cell wall mitogen, LPS, and chemotactic factors such as fMLP, C5a, and IL-8 all activate the ERK pathway. In addition, the ERK pathway is activated as a result of T cell receptor ligation with antigen or agents such as PMA/ionomycin or anti-CD3 antibody, which mimic TCR ligation in T cells (*Proc. Natl. Acad. Sci. USA* (1995) 92, 7686–7689). These findings indicate that inhibitors of the ERK pathway should function as anti-inflammatory and immune suppressive agents.

Small molecule inhibitors of the Raf/MEK/ERK pathway have been identified. A series of benzoquinones has been disclosed by Parke-Davis, which is exemplified by PD 098059 that inhibits MEK activity (*J. Biol. Chem.* (1995) 46, 27498–27494). Recently, we identified a MEK inhibitor, U0126 (*J. Biol. Chem.* (1998) 29, 18623–18632). Comparative kinetic analysis showed that U0126 and PD 098059 were non-competitive inhibitors of activated MEK (*J. Biol. Chem.* (1998) 29, 18623–18632). These MEK inhibitors have been used to investigate the role of the ERK activation cascade in a wide variety of systems including inflammation, immune suppression and cancer. For example, PD 098059 blocks thymidine incorporation into DNA in PDGF-stimulated Swiss 3T3 cells (*J. Biol. Chem.* (1995) 46, 27498–27494). PD 098059 also prevents PDGF-BB-dependent SMC (Smooth Muscle Cell) chemotaxis at concentrations which inhibit ERK activation (*Hypertension* (1997) 29, 334–339). Similarly, U0126 prevents PDGF-dependent growth of serum starved SMC. We have also shown that U0126 blocks keratinocyte proliferation in response to a pituitary growth factor extract, which consists primarily of FGF. These data coupled with those obtained with PD 098059 above indicate that MEK activity is essential for growth factor-stimulated proliferation.

The role of the MEK/ERK pathway in inflammation and immune suppression has been examined in a number of systems, including models of T cell activation. The T cell antigen receptor (TCR) is a non-RTK receptor whose intracellular signaling pathways have been elucidated (*Proc. Natl. Acad. Sci. USA* (1995) 92, 7686–7689). DeSilva et al. have generated a great deal of information with U0126 in T cell systems (*J. Immunol.* (1998) 160, 4175–4181). Their data showed that U0126 prevents ERK activation in T cells in response to PMA/ionomycin, Con A stimulation, and antigen in the presence of costimulation. In addition, T cell activation and proliferation in response TCR engagement is blocked by U0126 as is IL-2 synthesis. These results indicate that MEK inhibition does not result in a general antiproliferative effect in this IL-2-driven system, but selectively blocks components of the signaling cascades initiated by T cell receptor engagement.

PD 098059 has also been shown to inhibit T cell proliferation in response to anti-CD3 antibody, which is reversed by IL-2 (*J. Immunol.* (1998) 160, 2579–2589). PD 098059 also blocked IL-2 production by T cells stimulated with anti-CD3 antibody in combination with either anti-CD28 or PMA. In addition, the MEK inhibitor blocked TNFa, IL-3 GM-CSF, IFN-g, IL-6 and IL-10 production. In contrast, PD 098059 enhanced production of IL-4, IL-5 and IL-13 in similarly stimulated T cell cultures. These differential T cells effects with MEK inhibition suggest that therapeutic manipulations may be possible.

Neutrophils show ERK activation in response to the agonists N-formyl peptide (fMLP), IL-8, C5a and LTB$_4$, which is blocked by PD 098059 (*Biochem. Biophy. Res. Commun.* (1997) 232, 474–477). Additionally, PD 098059 blocks neutrophil chemotaxis in response to all agents, but does not alter superoxide anion production. However, fMLP-stimulated superoxide generation was inhibited by PD098059 in HL-60 cells (*J. Immunol.* (1997) 159, 5070–5078), suggesting that this effect may be cell-type specific. U0126 blocks ERK activation in fMLP- and LTB$_4$-stimulated neutrophils, but does not impair NADPH-oxidase activity or bacterial cell killing. U0126 at 10 mM blunts up regulation of b2 integrin on the cell surface by 50% and blocks chemotaxis through a fibrin gel >80% in response to IL-8 and LTB$_4$. Thus, neutrophil mobility is affected by MEK inhibition although the acute functional responses of the cell remain intact.

Eicosanoids are key mediators of the inflammatory response. The proximal event leading to prostaglandin and leukotriene biosynthesis is arachidonic acid release from membrane stores, which is mediated largely through the action of cytosolic phospholipase $A_2$ (c$PLA_2$). Activation of c$PLA_2$ requires $Ca^{2+}$ along with phosphorylation on a consensus MAP kinase site, $Ser^{505}$, which increases catalytic efficiency of the enzyme (*J. Biol. Chem.* (1997) 272, 16709–16712). In neutrophils, mast cells, or endothelial cells, PD 098059 blocks arachidonic acid release in response to opsonized zymosan, aggregation of the high affinity IgG receptor, or thrombin, respectively. Such data support a role for ERK as the mediator of c$PLA_2$ activation through phosphorylation (*FEBS Lett.* (1996) 388, 180–184; *Biochem J.* (1997) 326, 867–876; and *J. Biol. Chem.* (1997) 272, 13397–13402). Similarly, U0126 is able to block arachidonic acid release along with prostaglandin and leukotriene synthesis in keratinocytes stimulated with a variety of agents. Thus, the effector target, cPLA2, is sensitive to MEK inhibition in a variety of cell types.

MEK inhibitors also seem to affect eicosanoid production through means other than inhibition of arachidonic acid release. PD 098059 partially blocked LPS-induced Cox-2 expression in RAW 264.7 cells, indicating ERK activation alone may not be sufficient to induce expression of this key enzyme mediating inflammatory prostanoid production (*Biochem J.* (1998) 330, 1107–1114). Similarly, U0126 inhibits Cox-2 induction in TPA-stimulated fibroblasts, although it does not impede serum induction of the Cox-2 transcript. PD 098059 also inhibits Cox-2 induction in lysophosphatidic acid (LPA)-stimulated rat mesangial cells, which further supports a role for ERK activation in production of prostaglandins (*Biochem J.* (1998) 330, 1107–1114). Finally, 5-lipoxygenase translocation from the cytosol to the nuclear membrane along with its activation as measured by 5-HETE production can be inhibited by PD 098059 in HL-60 cells (*Arch. Biochem. Biophys.* (1996) 331, 141–144).

Inflammatory cytokines such as TNFa and IL-1b are critical components of the inflammatory response. Cytokine production in response to cell activation by various stimuli as well as their activation of downstream signaling cascades represent novel targets for therapeutics. Although the primary effect of IL-1b and TNF-a is to up-regulate the stress pathways (*Nature* (1994) 372, 729–746), published reports (*Proc. Natl. Acad. Sci. USA* (1995) 92, 1614–1618; *J. Immunol.* (1995) 155, 1525–1533; *J. Biol. Chem.* (1995) 270, 27391–27394. *Eur. J. Biochem.* (1995) 228, 1–15.). Cytokines such as TNFa and IL-1b, the bacterial cell wall mitogen, LPS, and chemotactic factors such as fMLP, C5a, and IL-8 all activate the ERK pathway. In addition, the ERK pathway is activated as a result of T cell receptor ligation with antigen or agents such as PMA/ionomycin or anti-CD3 antibody, which mimic TCR ligation in T cells (*Proc. Natl. Acad. Sci. USA* (1995) 92, 7686–7689) and clearly show that the ERK pathway is also affected. U0126 can block MMP induction by IL-1b and TNF-a in fibroblasts (*J. Biol. Chem.* (1998) 29, 18623–18632), demonstrating that ERK activation is necessary for this proinflammatory function. Similarly, lipopolysaccharide (LPS) treatment of monocytes results in cytokine production that has been shown to be MAP kinase-dependent being blocked by PD 098059 (*J. Immunol.* (1998) 160, 920–928). Indeed, we have observed similar results in freshly isolated human monocytes and THP-1 cells where LPS-induced cytokine production is inhibitable by U0126 (*J. Immunol.* (1998) 161:5681–5686).

The proximal involvement of RAS in the activation of the ERK pathway suggests that MEK inhibition might show efficacy in models where oncogenic RAS is a determinant in the cancer phenotype. Indeed, PD 098059 (*J. Biol. Chem.* (1995) 46, 27498–27494) as well as U0126 are able to impede the growth of RAS-transformed cells in soft agar even though these compounds show minimal effects on cell growth under normal culture conditions. We have further examined the effects of U0126 on the growth of human tumor cell lines in soft agar. We have shown that U0126 can prevent cell growth in some cells, but not all, suggesting that a MEK inhibitor may be effective in only certain kinds of cancer. In addition, PD 098059 has been shown to reduce urokinase secretion controlled by growth factors such as EGF, TGFa and FGF in an autocrine fashion in the squamous cell carcinoma cell lines UM-SCC-1 and MDA-TV-138 (*Cancer Res.* (1996) 56, 5369–5374). In vitro invasiveness of UM-SCC-1 cells through an extracellular matrix-coated porous filter was blocked by PD 098059 although cellular proliferation rate was not affected. These results indicate that control of the tumor invasive phenotype by MEK inhibition may also be a possibility. The observed effects with PD 098059 and U0126 suggest that MEK inhibition may have potential for efficacy in a number of disease states. Our own data argue strongly for the use of MEK inhibitors in T cell mediated diseases where immune suppression would be of value. Prevention of organ transplant rejection, graft versus host disease, lupus erythematosus, multiple sclerosis, and rheumatoid arthritis are potential disease targets. Effects in acute and chronic inflammatory conditions are supported by the results in neutrophils and macrophage systems where MEK inhibition blocks cell migration and liberation of proinflammatory cytokines. A use in conditions where neutrophil influx drives tissue destruction such as reperfusion injury in myocardial infarction and stroke as well as inflammatory arthritis may be warranted. Blunting of SMC migration and inhibition of DNA replication would suggest atherosclerosis along with restenosis following angioplasty as disease indications for MEK inhibitors. Skin disease such as psoriasis provides another potential area where MEK inhibitors may prove useful since MEK inhibition prevents skin edema in mice in response to TPA. MEK inhibition also blocks keratinocyte responses to growth factor cocktails, which are known mediators in the psoriatic process. Finally, the use of a MEK inhibitor in cancer can not be overlooked. Ionizing radiation initiates a process of apoptosis or cell death that is useful in the treatment solid tumors. This process involves a balance between pro-apoptotic and anti-apoptotic signal (*Science* 239, 645647), which include activation of MAP kinase cascades. Activation of the SAPK pathway delivers a pro-apoptotic signal (*Radiotherapy and Oncology* (1998) 47, 225–232.), whereas activation of the MAPK pathway is anti-apoptotic (*Nature* (1996) 328, 813–816.). Interference with the anti-apoptotic MAPK pathway by dominant negative MEK2 or through direct inhibition of MEK with synthetic inhibitors sensitizes cells to radiation-induced cell death (*J. Biol. Chem.* (1999) 274, 2732–2742; and *Oncogene* (1998) 16, 2787–2796). Thus, a MEK would be useful as a radiosensitizer in the treatment of solid tumors.

U.S. Pat. No. 5,099,021 describes a process for the preparation of unsymmetrically disubstituted ureas, but does not include an adamantyl moiety.

SUMMARY OF THE INVENTION

Accordingly, one object of the invention is to provide the compound N-adamant-1-yl-N'-[4-chlorobenzothiazol-2-yl] urea, pharmaceutically acceptable prodrug and salt forms thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating a disorder involving MEK, comprising: administering to a host in need of such treatment a therapeutically effective amount of at least one of the compounds of the present invention or a pharmaceutically acceptable salt or prodrug form thereof.

It is another object of the present invention to provide a novel method of using the compounds of the present invention as a radiosensitizing agent for the treatment of cancers or proliferative diseases, comprising: administering to a host in need of such treatment a therapeutically effective amount of a compound of the present invention, or a pharmaceutically acceptable prodrug or salt form thereof.

It is another object of the present invention to provide a novel method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of formula (I) or a pharmaceutically acceptable salt form thereof.

It is another object of the present invention to provide a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula (I) or a pharmaceutically acceptable salt form thereof.

It is another object of the present invention to provide novel amino-thio-acrylonitriles or salts or prodrugs thereof for use in therapy.

It is another object of the present invention to provide the use of novel amino-thio-acrylonitriles or salts or prodrugs thereof for the manufacture of a medicament for the treatment of an inflammatory disease.

It is another object of the present invention to provide the use of novel amino-thio-acrylonitriles or salts or prodrugs thereof for the manufacture of a medicament for the treatment of cancer.

These and other objects, which will become apparent during the following detailed description, have been achieved by the inventors' discovery that the compound of the present invention, stereoisomeric forms, mixtures of stereoisomeric forms, or pharmaceutically acceptable prodrug or salt forms thereof, is an effective inhibitor of inflammation.

DETAILED DESCRIPTION OF THE INVENTION

Thus, in a first embodiment of the present invention the compound N-adamant-1-yl-N'-[4-chlorobenzothiazol-2-yl] urea, can be made by the reactions described in Scheme 1. Reaction of the 2-amino-4-chlorobenzothiazole 1 with the carbamoyl chloride of adamantamine (2) yields urea 3 (for reactions of carbamoyl chlorides, see Wolf, F. J. et al., *J. Am. Chem. Soc.* (1954), 76, 256; Carter, H. E.; Frank, R. L.; Johnston, H. W.; *Org. Synth.* (1943), 23). The above sequence can also be reversed so that adamantamine 5 can react with the carbamoyl chloride of 2-amino-4-chlorobenzothiazole 4 to yield urea 3. Carbamoyl chlorides can be synthesized by the method of Hintze, F., and Hoppe, D. (*Synthesis* (1992) 12, 1216–1218).

2-Amino-4-chlorobenzothiazole 1 can also be reacted with 1-adamantylisocyanate 6 to yield urea 3 and the sequence can also be performed in reverse (7+5 yielding 3). Isocyanates may be synthesized by the following methods including, but not limited to, Nowakowski, J. J. Prakt, *Chem./Chem-Ztg.* (1996), 338, 7, 667–671; Knoelker, H.-J. et al., *Angew. Chem.* (1995), 107, 22, 2746–2749; Nowick, J. S. et al., *J. Org. Chem.* (1996), 61, 11, 3929–3934; Staab, H. A.; Benz, W.; *Angew. Chem.* (1961), 73).

Reaction of 4-chloro-2-aminobenzothiazole with a chloroformate such as o-, p-nitrophenylchloroformate, 4-chlorophenylchloroformate, 4-methylsulfonylphenylchloroformate, pentafluorophenylchloroformate, or phenylchloroformate in an inert solvent such as THF at a temperature anywhere from $-78°$ C. to room temperature yields the corresponding phenylcarbamate 7: (p-NO2: Tabuchi, S., et al., *Bioorg. Med. Chem. Lett.*, (1997), 7, 2, 169–174.; phenyl: Lyon, P. A.; Reese, C. B.; *J. Chem. Soc., Perkin Trans.* 1 (1978); 4-chloro: Iwakura, Y.; Nishiguchi, T.; Nabeya, A.; *J. Org. Chem.* (1966), 31); 4-methylsulfonyl: Freer, R. et al., *Synth. Commun.* (1996), 26, 2, 331–349; pentafluoro: Han, H., et al., *J. Am. Chem. Soc.* (1996), 118, 11, 2539–2544). All of the above carbamates can also be synthesized from the corresponding phenol and the carbamoyl chloride of 2-amino-4-chlorobenzothiazole (Crounse, N. N.; Raiford, L. C.; *J. Org. Chem.* (1945), 10). Displacement of the intermediate carbamate with adamantanamine 5 yields the corresponding urea 3. The above sequence can be reversed so that reaction of adamantamine 5 with a chloroformate such as o-, p-nitrophenylchloroformate, 4-chlorophenyl chloroformate, 4-methylsulfonylphenylchloroformate, pentafluorophenylchloroformate, or phenylchloroformate in an inert solvent such as THF at a temperature anywhere from $-78°$ C. to room temperature, yields intermediate carbamate 8. Further reaction with 2-amino-4-chlorobenzo thiazole yields the corresponding urea 3.

An additional reaction sequence that leads to urea 3 involves the reaction of carbonyldiimidazole (CDI) (Romine, J. L.; Martin, S. W.; Meanwell, N. A.; Epperson, J. R.; *Synthesis* (1994), 8, 846–850) with 1 followed by reaction of the intermediate imidazolide 9 with adamantanamine 5. The reaction may also be performed in the reversed sequence (adamantamine +CDI, followed by 2-amino-4-chlorobenzothiazole). Activation of imidazolide intermediates also facilitates urea formation (Bailey, R. A., et al., *Tet. Lett.* (1998), 39, 6267–6270).

The urea-forming reactions are performed in a non-hydroxylic inert solvent such as THF, toluene, DMF, methylene chloride, chloroform, carbon tetrachloride, and the like, at room temperature to the reflux temperature of the solvent and can employ the use of an acid scavenger or base when necessary such as carbonate and bicarbonate salts, triethylamine, DBU, Hunigs base, DMAP, and the like.

Scheme 1

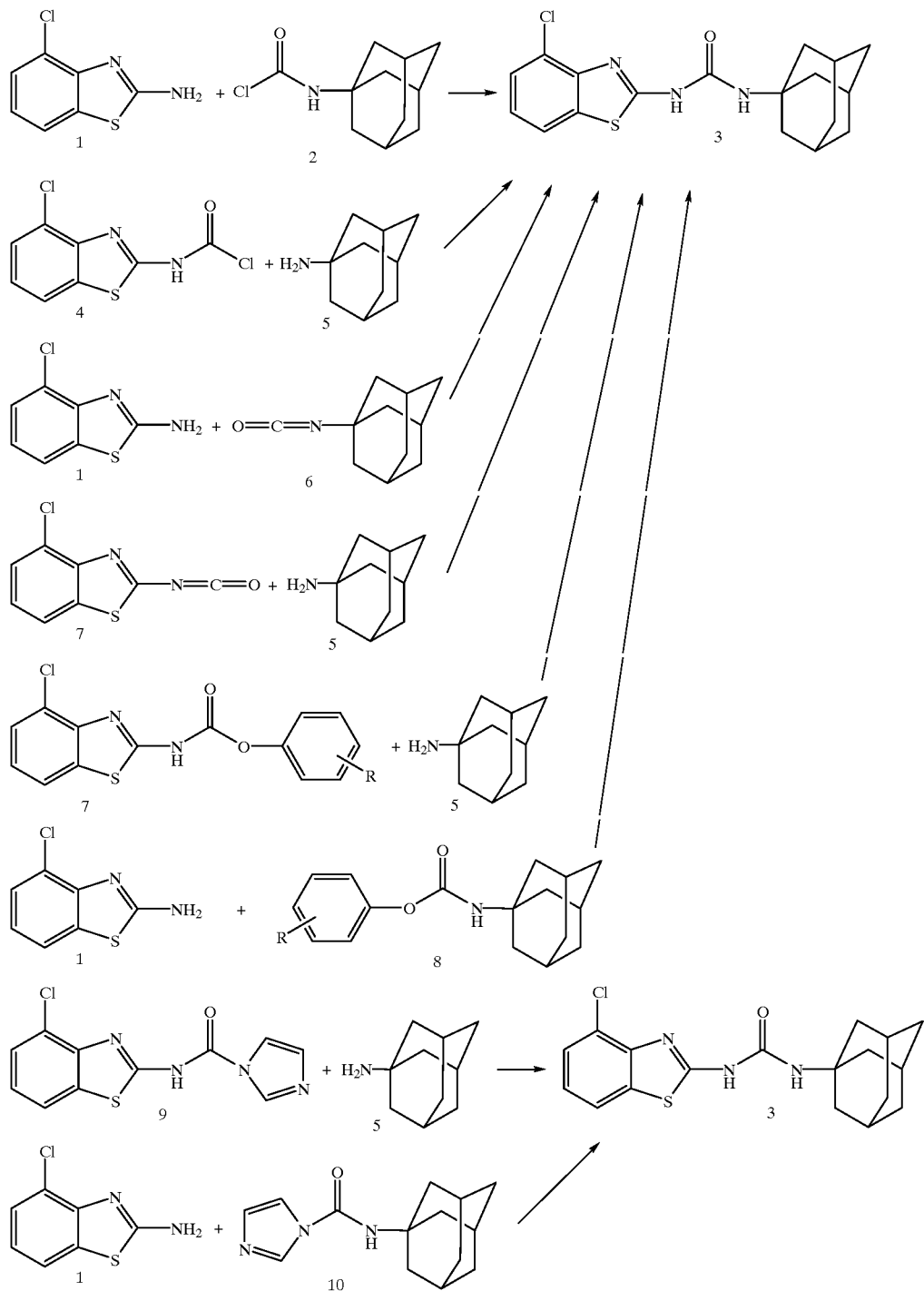

EXAMPLES

The terms and abbreviations used herein have their normal meanings unless otherwise designated. For example, "° C." refers to degrees Celsius; "N" refers to normal or normality; "mmole" refers to millimole or millimoles; "g" refers to gram or grams; and "M" refers to molar or molarity. The compound of this invention was prepared by the following procedure:

Preparation of N-adamant-1-yl-N'-(4-chlorobenzothiazol-2-yl)urea

Procedure A:

2-Amino-4-chlorobenzothiazole (200 mg, 1.08 mmol., 1 eq.), 1-adamantylisocyanate (191 mg, 1.08 mmol., 1 eq.) and THF (5 mL) were mixed and stirred at room temperature overnight. No reaction occurred and therefore two additional equivalents of 1-adamantylisocyanate were added and the mixture stirred at room temperature overnight. The mixture was then refluxed for 4 hours. The solvent was evaporated and ether was added. A white solid precipitated which was filtered and dried to yield 220 mg. The solid was chromatographed in 5 to 10% EtOAc in hexanes to yield 140 mg of a white solid. Recrystallization from methylcyclohexane yielded 105 mg of a white solid. The solid was re-chromatographed in 5 to 6 to 7% EtOAc in hexanes to yield 69 mg of a white solid (yield 18%). NMR ($_1$H, DMSO) δ10.82 (bs, 1H), 7.85 (d, 1H), 7.44 (d, 1H), 7.19 (dd, 1H), 6.39 (bs, 1H), 2.05 (bs, 3H), 1.99 (bs, 6H), 1.65 (bs, 6H). MS (ESI+): 361.8 (M+H). HRMS (CI+) Calc: 362.109387. Found:362.108395 (M+H).

Procedure B:

Part A. Preparation of N-(4-chlorobenzothiazol-2-yl)-O-phenylcarbamate

2-Amino-4-chlorobenzothiazole (10.00 g, 54.2 mmol., 1 eq.) was suspended in methylene chloride at room temperature with stirring. Triethylamine (9.81 mL, 70.4 mmol., 1.3 eq.) was added and the suspension cooled to 0° C. Phenyl chloroformate (8.83 mL, 70.4 mmol., 1.3 eq.) was then added dropwise. By the end of addition, the mixture became an amber solution. After 5 minutes, a precipitate began to form. TLC showed reaction essentially complete after 1.5 hours. Water was added and the insoluble material filtered. The filtrate was added to a separatory funnel, and the layers separated. The organic layer was washed with water (2×), dried (MgSO4) and the solvent removed in vacuo to yield a yellow solid. These solids were stirred in ether/hexanes (1:1) (100 mL) and filtered. The filter cake was rinsed with hexanes and pumped dry under high vacuum to yield 11.45 g of white solids consisting of product and a minor impurity. The compound was used as is for the subsequent step. NMR (DMSO-d6) δ:13.00–12.50 (m, 1H); 7.97 (d, 1H); 7.60–7.40 (m, 3H); 7.40–7.20 (m, 4H).

Part B. Preparation of N-adamant-1-yl-N'-(4-chlorobenzothiazol-2-yl) urea

N-(4-chlorobenzothiazol-2-yl)-O-phenylcarbamate (15.0 g, 49.2 mmol., 1 eq.), 1-adamantanamine (7.44 g, 49.2 mmol., 1 eq.) and THF (200 mL) were mixed and refluxed overnight. The mixture was cooled, some silica gel added, and the mixture evaporated to dryness. The powder containing the crude reaction product on silica gel was added to a silica gel column and flash chromatographed in 10% EtOAc/hexanes to 30% EtOAc/hexanes, to 25% EtOAc/25% THF/50% hexanes to yield 11.0 g of a white solid. Crystallization from EtOH yielded 6.8 g of a first crop and 1.0 g of a second crop. M.P. first crop: 229.0° C. M. P. second crop:228.5–229.5° C. All spectral data were identical to the data listed above.

In another embodiment, the present invention provides novel pharmaceutical compositions, comprising: a pharmaceutically acceptable carrier and a therapeutically effective amount of N-adamant-1-yl-N'-[4-chlorobenzothiazol-2-yl] urea, or a pharmaceutically acceptable salt form thereof.

In another embodiment, the present invention provides a novel process for treatment of an inflammatory disease, comprising: administering to a host in need of such treatment a therapeutically effective amount of N-adamant-1-yl-N'-[4-chlorobenzothiazol-2-yl] urea, or a pharmaceutically acceptable salt form thereof.

In another embodiment, the present invention provides a novel method for treating cancer or proliferative diseases by radiosensitization, comprising: administering to a host in need of such treatment a therapeutically effective amount of N-adamant-1-yl-N'-[4-chlorobenzothiazol-2-yl] urea or a pharmaceutically acceptable salt form thereof.

In another embodiment, the present invention provides N-adamant-1-yl-N'-[4-chlorobenzothiazol-2-yl] urea or a pharmaceutically acceptable salt form thereof for the manufacture of a medicament for the treatment of an inflammatory disease.

In another embodiment, the present invention provides N-adamant-1-yl-N'-[4-chlorobenzothiazol-2-yl] urea or a pharmaceutically acceptable salt form thereof for the manufacture of a medicament for the treatment of cancer or a proliferative disease.

In another embodiment, the present invention provides N-adamant-1-yl-N'-[4-chlorobenzothiazol-2-yl] urea or a pharmaceutically acceptable salt form thereof for use in therapy.

As used herein, "pharmaceutically acceptable salts" refer to derivatives of the disclosed compound wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p.1445, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers which release the active parent drug in vivo when such prodrug is administered to a mammalian subject. Prodrugs of a compound are prepared by modifying functional groups present in the compound in such a way that the modifications are cleaved, either in routine manipulation or in vivo, to the parent compound.

"Therapeutically effective" amount is intended to include an amount of a compound or an amount of a combination of compounds claimed effective to inhibit inflammation or treat the symptoms of inflammation in a host. The combination of compounds is preferably a synergistic combination. Synergy, as described for example by Chou and Talalay, *Adv.*

*Enzyme Regul.* 22:27–55 (1984), occurs when the effect (in this case, reduction or prevention of inflammation) of the compounds when administered in combination is greater than the additive effect of the compounds when administered alone as a single agent. In general, a synergistic effect is most clearly demonstrated at suboptimal concentrations of the compounds. Synergy can be in terms of less inflammation or some other non-additive beneficial effect of the combination compared with the individual components.

The term "radiosensitize", as used herein refers to a process whereby cells are made susceptible to radiation-induced cell death, or the cells that result from this process.

Dosage and Formulation

The inflammation-inhibiting/cancer-treating compound of the present invention can be administered in such oral dosage forms as tablets, capsules (each of which includes sustained release or timed release formulations), pills, powders, granules, elixirs, tinctures, suspensions, syrups, and emulsions. The compound of the present invention can also be administered in intravenous (bolus or infusion), intraperitoneal, subcutaneous, or intramuscular form, all using dosage forms well known to those of ordinary skill in the pharmaceutical arts. The compound can be administered alone, but generally will be administered with a pharmaceutical carrier selected on the basis of the chosen route of administration and standard pharmaceutical practice.

The dosage regimen for the compound of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. The compound of this invention may be administered in a single daily dose, or the total daily dosage may be administered in divided doses of two, three, or four times daily.

The compound of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compound is typically administered in admixture with suitable pharmaceutical diluents, excipients, or carriers (collectively referred to herein as pharmaceutical carriers) suitably selected with respect to the intended form of administration, that is, oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as ethanol, glycerol, and water. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrators include, but are not limited to, starch, methyl cellulose, agar, bentonite, and xanthan gum.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compound of the present invention may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compound of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compound of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Obviously, numerous modifications and variations of the present invention are possible in light of the above teachings. It is therefore understood that within the scope of the appended claims, the invention may be practiced otherwise than as specifically described herein.

What is claimed is:

1. A compound, N-Adamant-1-yl-N'-[4-Chlorobenzothiazol-2-yl] Urea.

2. A pharmaceutical composition, comprising: a pharmaceutically acceptable carrier and a therapeutically effective amount of a compound of claim 1 or a pharmaceutically acceptable salt form thereof.

3. A method for treating or preventing a disorder related to MEK, comprising: administering to a patient in need thereof a therapeutically effective amount of a compound of claim 1 or a pharmaceutically acceptable salt form thereof.

4. A compound of claim 1 or a pharmaceutically acceptable salt form thereof for use in therapy.

5. A compound of claim 1 or a pharmaceutically acceptable salt form thereof for the manufacture of a medicament for the treatment of an disorder related to MEK.

6. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of claim 1 or a pharmaceutically acceptable salt form thereof.

7. A method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 1 or a pharmaceutically acceptable salt form thereof.

* * * * *